US009322969B2

(12) United States Patent
Burov et al.

(10) Patent No.: US 9,322,969 B2
(45) Date of Patent: Apr. 26, 2016

(54) HYDROGEN-SENSING OPTICAL FIBER HYDROGEN-PASSIVATED TO PREVENT IRREVERSIBLE REACTIONS WITH HYDROGEN AND HYDROGEN-INDUCED ATTENUATION LOSSES

(71) Applicant: Draka Comteq, B.V., Amsterdam (NL)

(72) Inventors: Ekaterina Burov, Boulogne-Billancourt (FR); Alain Pastouret, Massy (FR); Gilles Melin, Orsay (FR)

(73) Assignee: Draka Comteq, B.V., Amsterdam (NL)

( * ) Notice: Subject to any disclaimer, the term of this patent is extended or adjusted under 35 U.S.C. 154(b) by 420 days.

(21) Appl. No.: 13/657,251

(22) Filed: Oct. 22, 2012

(65) Prior Publication Data

US 2013/0175437 A1    Jul. 11, 2013

(30) Foreign Application Priority Data

Oct. 20, 2011   (EP) .................................... 11306358

(51) Int. Cl.
| | | |
|---|---|---|
| *F21V 8/00* | (2006.01) | |
| *G01N 21/25* | (2006.01) | |
| *G01N 33/00* | (2006.01) | |
| *G01N 21/77* | (2006.01) | |

(52) U.S. Cl.
CPC ............ *G02B 6/0001* (2013.01); *G01N 21/255* (2013.01); *G01N 21/7703* (2013.01); *G01N33/005* (2013.01); *G01N 2021/7709* (2013.01); *G01N 2021/7783* (2013.01); *G01N 2201/0886* (2013.01)

(58) Field of Classification Search
CPC ... G01D 5/353; G01D 5/35303; G01D 5/268; G01D 5/32; G01V 8/16; G01V 8/20; G01V 8/12; G02B 6/02; G02B 6/02171; G02B 2006/12038; G02B 2006/12061; G01N 21/01; G01N 21/17; G01N 21/25; G01N 21/27; G01N 21/274; G01N 21/31; G01N 21/4133; G01N 21/84; G01N 2021/0106; G01N 2021/1748; G01N 2021/1765; G01N 2021/1793; G01N 2021/1795; G01N 2021/4166; G01N 2021/8411; G01N 2021/8528; G01N 21/85; G01N 21/8507; G01N 2021/8578; C03B 37/027; C03B 37/01446

USPC .................... 250/227.18, 227.14, 222.2, 221; 385/12, 123; 356/128, 130–132, 432, 356/433, 436–439; 65/376–378, 424, 426; 264/1.24

See application file for complete search history.

(56) References Cited

U.S. PATENT DOCUMENTS

| | | | |
|---|---|---|---|
| 4,838,643 | A | 6/1989 | Hodges et al. |
| 5,153,931 | A | 10/1992 | Buchanan et al. |

(Continued)

FOREIGN PATENT DOCUMENTS

| | | |
|---|---|---|
| EP | 1921478 A1 | 5/2008 |
| EP | 2584340 A1 | 4/2013 |

(Continued)

OTHER PUBLICATIONS

European Search Report in counterpart European Application No. 11306358.0 dated Mar. 30, 2013, pp. 1-10.

*Primary Examiner* — Que T Le
(74) *Attorney, Agent, or Firm* — Additon, Higgins & Pendleton, P.A.

(57) ABSTRACT

In harsh and hazardous environments, the presence of elevated levels of hydrogen gas is an indicator of chemical and/or radiological activity. The present hydrogen-sensing optical fiber provides rapid and reliable hydrogen detection and quantification, irrespective of temperature fluctuations. The hydrogen-sensing optical fiber does not exhibit significant irreversible hydrogen-induced attenuation losses after exposure to a hydrogen-rich atmosphere.

21 Claims, 8 Drawing Sheets

(56) References Cited

U.S. PATENT DOCUMENTS

| | | |
|---|---|---|
| 5,574,816 A | 11/1996 | Yang et al. |
| 5,717,805 A | 2/1998 | Stulpin |
| 5,761,362 A | 6/1998 | Yang et al. |
| 5,783,152 A | 7/1998 | Nave |
| 5,911,023 A | 6/1999 | Risch et al. |
| 5,982,968 A | 11/1999 | Stulpin |
| 6,035,087 A | 3/2000 | Bonicel et al. |
| 6,066,397 A | 5/2000 | Risch et al. |
| 6,085,009 A | 7/2000 | Risch et al. |
| 6,134,363 A | 10/2000 | Hinson et al. |
| 6,175,677 B1 | 1/2001 | Yang et al. |
| 6,181,857 B1 | 1/2001 | Emeterio et al. |
| 6,210,802 B1 | 4/2001 | Risch et al. |
| 6,215,931 B1 | 4/2001 | Risch et al. |
| 6,314,224 B1 | 11/2001 | Stevens et al. |
| 6,321,012 B1 | 11/2001 | Shen |
| 6,321,014 B1 | 11/2001 | Overton et al. |
| 6,334,016 B1 | 12/2001 | Greer, IV |
| 6,381,390 B1 | 4/2002 | Hutton et al. |
| 6,493,491 B1 | 12/2002 | Shen et al. |
| 6,499,318 B1* | 12/2002 | Lemaire et al. ............... 65/379 |
| 6,603,908 B2 | 8/2003 | Dallas et al. |
| 6,618,538 B2 | 9/2003 | Nechitailo et al. |
| 6,658,184 B2 | 12/2003 | Bourget et al. |
| 6,709,997 B2* | 3/2004 | Urano ............... C03B 19/1453 385/115 |
| 6,749,446 B2 | 6/2004 | Nechitailo |
| 6,853,798 B1* | 2/2005 | Weiss ............................ 385/142 |
| 6,912,347 B2 | 6/2005 | Rossi et al. |
| 6,922,515 B2 | 7/2005 | Nechitailo et al. |
| 6,941,049 B2 | 9/2005 | Risch et al. |
| 7,045,010 B2 | 5/2006 | Sturman, Jr. |
| 7,162,128 B2 | 1/2007 | Lovie et al. |
| 7,257,301 B2* | 8/2007 | Homa ............... C03C 13/046 385/123 |
| 7,322,122 B2 | 1/2008 | Overton et al. |
| 7,346,244 B2 | 3/2008 | Gowan et al. |
| 7,356,234 B2 | 4/2008 | de Montmorillon et al. |
| 7,483,613 B2 | 1/2009 | Bigot-Astruc et al. |
| 7,515,795 B2 | 4/2009 | Overton et al. |
| 7,526,177 B2 | 4/2009 | Matthijsse et al. |
| 7,555,186 B2 | 6/2009 | Flammer et al. |
| 7,567,739 B2 | 7/2009 | Overton et al. |
| 7,570,852 B2 | 8/2009 | Nothofer et al. |
| 7,587,111 B2 | 9/2009 | de Montmorillon et al. |
| 7,599,589 B2 | 10/2009 | Overton et al. |
| 7,623,747 B2 | 11/2009 | de Montmorillon et al. |
| 7,639,915 B2 | 12/2009 | Parris et al. |
| 7,646,952 B2 | 1/2010 | Parris |
| 7,646,954 B2 | 1/2010 | Tatat |
| 7,702,204 B2 | 4/2010 | Gonnet et al. |
| 7,724,998 B2 | 5/2010 | Parris et al. |
| 7,792,392 B2* | 9/2010 | Chen et al. ..................... 385/12 |
| 7,817,891 B2 | 10/2010 | Lavenne et al. |
| 7,889,960 B2 | 2/2011 | de Montmorillon et al. |
| 7,970,247 B2 | 6/2011 | Barker |
| 7,974,507 B2 | 7/2011 | Lovie et al. |
| 7,995,888 B2 | 8/2011 | Gholami et al. |
| 8,009,950 B2 | 8/2011 | Molin et al. |
| 8,031,997 B2 | 10/2011 | Overton |
| 8,041,167 B2 | 10/2011 | Overton |
| 8,041,168 B2 | 10/2011 | Overton |
| 8,041,172 B2 | 10/2011 | Sillard et al. |
| 8,055,111 B2 | 11/2011 | Sillard et al. |
| 8,081,853 B2 | 12/2011 | Overton |
| 8,145,025 B2 | 3/2012 | de Montmorillon et al. |
| 8,145,026 B2 | 3/2012 | Overton et al. |
| 8,165,439 B2 | 4/2012 | Overton |
| 8,195,018 B2 | 6/2012 | Overton et al. |
| 8,259,389 B2 | 9/2012 | Pastouret et al. |
| 8,265,442 B2 | 9/2012 | Overton |
| 8,274,647 B2 | 9/2012 | Gholami et al. |
| 8,280,213 B2 | 10/2012 | Molin et al. |
| 8,290,324 B2 | 10/2012 | Sillard et al. |
| 8,301,000 B2 | 10/2012 | Sillard et al. |

| | | |
|---|---|---|
| 2002/0061810 A1* | 5/2002 | Urano ............... C03B 19/1453 501/54 |
| 2003/0044144 A1* | 3/2003 | Nelson ............... C03C 13/045 385/123 |
| 2004/0047576 A1 | 3/2004 | Kurusu et al. |
| 2005/0118064 A1 | 6/2005 | Berg |
| 2008/0292262 A1 | 11/2008 | Overton et al. |
| 2009/0129721 A1 | 5/2009 | Chen et al. |
| 2009/0214167 A1 | 8/2009 | Lookadoo et al. |
| 2009/0297107 A1 | 12/2009 | Tatat |
| 2010/0021170 A1 | 1/2010 | Lumineau et al. |
| 2010/0092135 A1 | 4/2010 | Barker et al. |
| 2010/0119202 A1 | 5/2010 | Overton |
| 2010/0135627 A1 | 6/2010 | Pastouret et al. |
| 2010/0142033 A1 | 6/2010 | Regnier et al. |
| 2010/0142969 A1 | 6/2010 | Gholami et al. |
| 2010/0150505 A1 | 6/2010 | Testu et al. |
| 2010/0154479 A1 | 6/2010 | Milicevic et al. |
| 2010/0166375 A1 | 7/2010 | Parris |
| 2010/0183821 A1 | 7/2010 | Hartsuiker et al. |
| 2010/0189397 A1 | 7/2010 | Richard et al. |
| 2010/0202741 A1 | 8/2010 | Ryan et al. |
| 2010/0214649 A1 | 8/2010 | Burov et al. |
| 2010/0215328 A1 | 8/2010 | Tatat et al. |
| 2010/0310218 A1 | 12/2010 | Molin et al. |
| 2011/0026889 A1 | 2/2011 | Risch et al. |
| 2011/0058781 A1 | 3/2011 | Molin et al. |
| 2011/0064367 A1 | 3/2011 | Molin et al. |
| 2011/0064371 A1 | 3/2011 | Leatherman et al. |
| 2011/0069724 A1 | 3/2011 | Richard et al. |
| 2011/0069932 A1 | 3/2011 | Overton et al. |
| 2011/0091171 A1 | 4/2011 | Tatat et al. |
| 2011/0116160 A1 | 5/2011 | Bolvin et al. |
| 2011/0123162 A1 | 5/2011 | Molin et al. |
| 2011/0135262 A1 | 6/2011 | Molin et al. |
| 2011/0135263 A1 | 6/2011 | Molin et al. |
| 2011/0176782 A1 | 7/2011 | Parris |
| 2011/0188823 A1 | 8/2011 | Sillard et al. |
| 2011/0188826 A1 | 8/2011 | Sillard et al. |
| 2011/0199604 A1 | 8/2011 | Ramos |
| 2011/0217012 A1 | 9/2011 | Bigot-Astruc et al. |
| 2011/0228275 A1 | 9/2011 | Xia et al. |
| 2011/0229101 A1 | 9/2011 | de Montmorillon et al. |
| 2011/0268398 A1 | 11/2011 | Quinn et al. |
| 2011/0268400 A1 | 11/2011 | Lovie et al. |
| 2011/0287195 A1 | 11/2011 | Molin |
| 2012/0009358 A1 | 1/2012 | Gharbi et al. |
| 2012/0014652 A1 | 1/2012 | Parris |
| 2012/0040105 A1 | 2/2012 | Overton |
| 2012/0040184 A1 | 2/2012 | de Montmorillon et al. |
| 2012/0051703 A1 | 3/2012 | Bigot-Astruc et al. |
| 2012/0057833 A1 | 3/2012 | Tatat |
| 2012/0092651 A1 | 4/2012 | Molin et al. |
| 2012/0134376 A1 | 5/2012 | Burov et al. |
| 2012/0148206 A1 | 6/2012 | Bolvin et al. |
| 2012/0195549 A1 | 8/2012 | Molin et al. |
| 2012/0195561 A1 | 8/2012 | Molin et al. |
| 2012/0213483 A1 | 8/2012 | Risch et al. |
| 2012/0224254 A1 | 9/2012 | Burov et al. |
| 2012/0243843 A1 | 9/2012 | Molin et al. |
| 2012/0251062 A1 | 10/2012 | Molin et al. |
| 2012/0275751 A1 | 11/2012 | Krabshuis et al. |
| 2012/0301093 A1 | 11/2012 | Sillard et al. |
| 2012/0315006 A1 | 12/2012 | Bigot-Astruc et al. |
| 2013/0004135 A1 | 1/2013 | Bigot-Astruc et al. |
| 2013/0028564 A1 | 1/2013 | Molin et al. |
| 2013/0175437 A1 | 7/2013 | Burov et al. |

FOREIGN PATENT DOCUMENTS

| | | |
|---|---|---|
| JP | 61-066949 A | 4/1986 |
| JP | 63-249040 A | 10/1988 |
| WO | 00/05570 A1 | 2/2000 |
| WO | 03/056313 A1 | 7/2003 |
| WO | 2009/062131 A1 | 5/2009 |
| WO | 2009/067671 A1 | 5/2009 |
| WO | 2009/154216 A1 | 12/2009 |

* cited by examiner

HYDROGEN-SENSING OPTICAL FIBER HYDROGEN-PASSIVATED TO PREVENT IRREVERSIBLE REACTIONS WITH HYDROGEN AND HYDROGEN-INDUCED ATTENUATION LOSSES

CROSS-REFERENCE TO PRIORITY APPLICATION

This application hereby claims the benefit of pending European Application No. 11306358.0 (filed Oct. 20, 2011, at the European Patent Office), which is hereby incorporated by reference in its entirety.

FIELD OF INVENTION

The invention relates to hydrogen-sensing fibers and to hydrogen sensors that include one or more hydrogen-sensing fibers.

BACKGROUND

Some prior hydrogen sensors do not include hydrogen-sensing fibers, because they rely on other technologies. Such hydrogen sensors often do not present the same flexibility as compared with hydrogen sensors that are based on hydrogen-sensing fibers.

Other prior hydrogen sensors include hydrogen-sensing fibers. Such hydrogen sensors present some advantages, notably their ability to be distributed and deported sensing systems, but they are not as reliable and/or flexible. For example, such hydrogen sensors often present one or more of the following drawbacks: hydrogen-presence detection that is too imprecise; hydrogen-presence detection that is unreliable over extended periods; hydrogen-presence detection that presents too long of a response time and/or too much complexity.

For example, International Publication No. WO 2009/154216 A1, which is hereby incorporated by reference in its entirety, discloses a hydrogen-fiber-sensor system in which hydrogen detection is realized via a detection layer at the periphery of an optical fiber containing a platinum catalyst whose refractive index is modified by the presence of hydrogen. This patent publication discloses a complicated and costly optical-fiber structure that requires coating the optical fiber with platinum and tungsten oxide layers.

International Publication No. WO 2009/067671 A1 and its counterpart U.S. Patent Publication No. 2011/0199604, each of which is hereby incorporated by reference in its entirety, disclose a hydrogen-fiber-sensor system in which hydrogen detection is realized via modification of optical-fiber characteristics at one or more wavelengths in the presence of hydrogen. The disclosed hydrogen-fiber-sensor system is unreliable over time and has a long response time, especially in environments in which the temperature can vary greatly and unpredictably, because the phenomenon employed is the irreversible increase of attenuation due to irreversible increase of OH— peak (e.g., at 1380 nanometers).

International Publication No. WO 2003/056313 A1 and its counterpart U.S. Patent Publication No. 2005/0118064, each of which is hereby incorporated by reference in its entirety, disclose an irreversible reaction with a metallic catalyst on a fiber cladding, which increases optical-fiber attenuation. These patent publications disclose a complicated and costly fiber structure that uses a metallic catalyst.

Finally, U.S. Pat. No. 5,153,931, which is hereby incorporated by reference in its entirety, discloses hydrogen-presence detection by hydrogen adsorption on hydrogen-sensing fiber cladding. This patent discloses a hydrogen-sensing optical-fiber structure that is based on hydrogen adsorption of fiber cladding, which can merely detect hydrogen presence without reliably quantifying it.

Accordingly, there is a need for a hydrogen-sensing fiber and a hydrogen sensor that alleviates the foregoing disadvantages.

SUMMARY

Therefore, in a first aspect, the invention embraces a hydrogen-sensing optical fiber that includes an optical core and a surrounding cladding. The defects in the optical core (e.g., silica defects) and/or defects in the cladding are substantially hydrogen-passivated (e.g., hydrogen modified) such that exposing the hydrogen-sensing optical fiber to hydrogen gas does not cause further significant irreversible interactions between (i) the defects in the optical core and/or the defects in the cladding and (ii) hydrogen gas. Thereafter, at any wavelength, the hydrogen-sensing optical fiber does not exhibit significant irreversible hydrogen-induced attenuation losses after exposure to a hydrogen-rich atmosphere.

In a second aspect, the invention embraces a hydrogen sensor for detecting atmospheric hydrogen. The hydrogen sensor, which employs a hydrogen-sensing optical fiber, provides excellent hydrogen-detection accuracy, response, and reliability.

In a third aspect, the invention embraces detecting and quantifying atmospheric hydrogen using a hydrogen-sensing optical fiber.

In a fourth aspect, the invention embraces making a hydrogen-sensing fiber by passivating defects in an optical fiber (e.g., via hydrogen modification). In this regard, an optical fiber having an optical core and a surrounding cladding is saturated within a hydrogen-rich atmosphere for a period that is sufficient to substantially react the defects in the optical core and/or the cladding with hydrogen. Thereafter, the optical fiber is outgassed to remove unreacted hydrogen.

In a fifth aspect, the invention embraces making a hydrogen sensor for detecting atmospheric hydrogen using a hydrogen-sensing optical fiber. For example, the hydrogen-sensing optical fiber can be assembled into the hydrogen sensor's casing and/or cable structure.

The foregoing illustrative summary, as well as other exemplary objectives and/or advantages of the invention, and the manner in which the same are accomplished, are further explained within the following detailed description and its accompanying drawings.

DETAILED DESCRIPTION

In harsh and hazardous environments, the presence of elevated levels of hydrogen gas is an indicator of chemical and/or radiological activity.

Therefore, in one aspect, the invention embraces an optical fiber that detects the presence of hydrogen (e.g., atmospheric hydrogen). The optical fiber is pretreated (e.g., with hydrogen gas) before it is deployed in the field (e.g., as a component of a hydrogen sensor) to prevent irreversible reactions with hydrogen from occurring during hydrogen monitoring. The pretreated optical fiber provides rapid, accurate, and reliable hydrogen detection and quantification over several decades, irrespective of environmental changes (e.g., temperature fluctuations), and with minimal maintenance.

Figure 1:
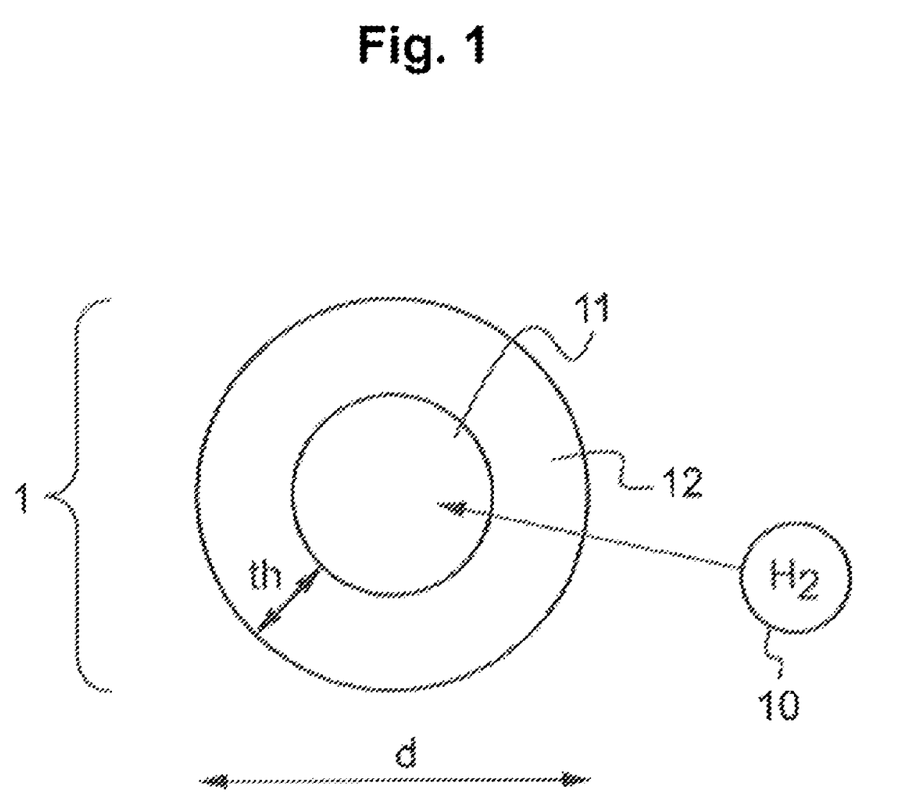
FIG. 1 schematically depicts an exemplary hydrogen-sensing optical fiber according to an embodiment of the present invention.

FIG. 1 schematically depicts an exemplary hydrogen-sensing optical fiber according to one embodiment of the present invention. The hydrogen-sensing optical fiber 1 (e.g., the "sensing fiber") includes an optical core 11 and a surrounding cladding 12. The sensing fiber 1 may also include one or more optical-fiber coatings around the cladding 12 to provide better protection. The sensing fiber 1 has a diameter (d) and a cladding thickness (th). When hydrogen 10 is present in the vicinity of the sensing fiber 1 (e.g., the sensing fiber 1 is positioned within a hydrogen-rich atmosphere), hydrogen 10 will diffuse over time from outside the sensing fiber 1 into the sensing fiber 1, first through any optical-fiber coating(s), then through the cladding 12, and finally into core 11 (i.e., toward the center of the optical fiber).

The sensing fiber 1 is pretreated to facilitate hydrogen diffusion into the core 11 (i.e., diffusion of atmospheric hydrogen 10 into the sensing fiber 1). The presence of hydrogen 10 in the sensing fiber 1, particularly the presence of hydrogen 10 in the core 11, causes measurable attenuation (e.g., reversible hydrogen-induced attenuation). This resulting attenuation indicates the presence of elevated atmospheric hydrogen 10. Thus, the more quickly hydrogen 10 can diffuse into the core 11—preferably the entire core 11, especially in center of the core 11—the shorter the response of the hydrogen-sensing fiber 1 (and the associated hydrogen sensor that includes sensing fiber 1).

To achieve the sensing fiber 1 (and as explained hereinafter), a suitable optical fiber (e.g., a multimode optical fiber or a single-mode optical fiber) is pretreated, typically with hydrogen. The optical fiber is pretreated with a gas (e.g., hydrogen gas) that is able to react with existing fiber glass defects to substantially passivate glass defects in the core 11 and/or the cladding 12. Thereafter, the optical fiber cannot undergo further significant irreversible hydrogen-induced losses at any wavelength, preferably for its lifetime. Substantially all irreversible interactions between sensing fiber 1 and hydrogen 10 occur during a pretreatment phase to yield the sensing fiber 1. When the resulting sensing fiber 1 is in use in the field, hydrogen 10 will diffuse more quickly into the core 11 (and to the core's center), because the previously reacted glass defects in the cladding 12 and/or the core 11 will no longer interact (and thereby impede) hydrogen diffusion within the sensing fiber 1. In sum, hydrogen pretreatment ensures that substantially all glass defects have already irreversibly reacted with hydrogen (e.g., the defects in the optical core 11 and/or the cladding 12 are substantially hydrogen-passivated) such that, during monitoring in the field, substantially no irreversible reactions with atmospheric hydrogen will occur.

It should be noted that pretreatment with deuterium is not recommended unless and until the sensing fiber 1 cannot undergo further irreversible hydrogen-induced losses, because hydrogen can replace deuterium (i.e., a hydrogen-deuterium exchange) if the sensing fiber 1 is exposed to hydrogen. This displacement of deuterium could cause deuterium rather than hydrogen to diffuse toward the center of the core 11. Within the core 11, deuterium would not have the same effect as hydrogen on optical-fiber attenuation.

The core 11 of the sensing fiber 1 is typically pure silica or silica doped with fluorine (e.g., a germanium-fluorine doped core). Co-doping using germanium and fluorine may help to reduce hydrogen-induced losses (HIL) (e.g., between 1385 nanometers and 1410 nanometers). A fluorine-doped core 11 is typically more robust in harsh and hazardous environments, such as within a radioactive environment (e.g., the underground storage of radioactive waste). In such harsh environments, a hydrogen leak is an indicator of a serious problem, such as corrosion of a metallic container storing hazardous materials or a reaction between leaking radioactive waste and the outside environment (e.g., water radiolysis). Moreover, there is an explosion risk at a hydrogen concentration exceeding about four weight percent.

Another exemplary radioactive environment is a nuclear power station. In such a radioactive environment, the shortened response time of the present sensing fiber is especially advantageous. Moreover, when the core of the sensing fiber is either undoped or doped with fluorine, the sensing fiber provides improved robustness as compared to an optical fiber that possesses a germanium-doped core. This is so because germanium tends to be much more sensitive to radiation.

To promote hydrogen diffusion into the core 11, the thickness (th) of the cladding 12 can be reduced (i.e., hydrogen can more quickly diffuse through a thin cladding 12 and an optional gas-permeable polymeric coating). That said, if the cladding 12 is made too thin or excluded altogether, the sensing fiber 1 might be insufficiently protected. By way of example, the cladding 12 typically has a thickness between about 5 microns and 60 microns (e.g., between about 10 microns and 30 microns). In addition, the cladding 12 may be made of a plastic material (e.g., the public material) rather than silica, because hydrogen diffuses more readily through lower-density polymer than through higher-density silica.

The sensing fiber 1 can be a multimode optical fiber with a relatively large core diameter d (e.g., a core of 50 microns or more, such as about 62.5 microns) or a single-mode optical fiber with a relatively small core diameter (e.g., a core of 10 microns or less, such as about 5 microns). In general, the presence of coating will slow down hydrogen diffusion into the optical fiber. A single-mode sensing fiber will require a relatively thicker coating due to its intrinsic brittleness, whereas a multimode sensing fiber will require a relatively thinner coating, if at all. Indeed, an exemplary sensing fiber is a coating-free multimode sensing fiber formed of a glass core and a surrounding polymeric cladding.

Figure 2:
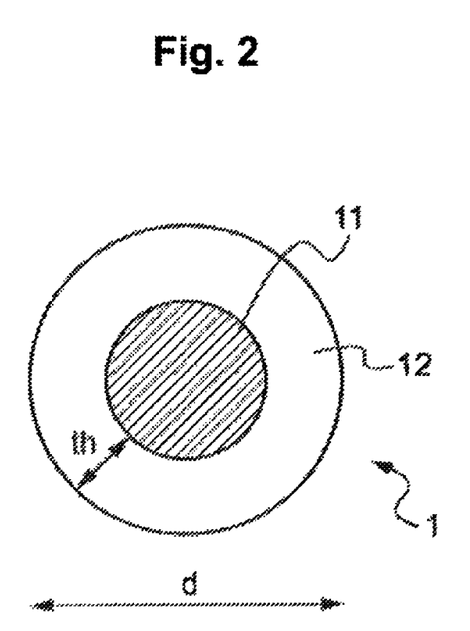
FIG. 2 schematically depicts an exemplary hydrogen-sensing optical fiber according to another embodiment of the present invention.

FIG. 2 schematically depicts an exemplary hydrogen-sensing, multimode optical fiber. This exemplary hydrogen-sensing, multimode fiber 1 includes a core 11, which might be formed of germanium and/or fluorine doped silica, and a cladding 12, which might be formed from a low-index polymer (e.g., having a refractive index of between about 1.36 and 1.46 at 850 nanometers). As depicted in FIG. 2, the exemplary multimode hydrogen-sensing fiber 1 has a diameter (d) and a cladding thickness (th). A typical outer diameter (d) is between about 30 microns and 150 microns, more typically between about 30 microns and 80 microns. A typical cladding thickness (th) is between about 10 microns and 50 microns, more typically between about 10 microns and 30 microns (e.g., 15-20 microns). As noted, a multimode hydrogen-sensing fiber might optionally include one or more thin fiber coatings (e.g., primary and secondary coatings) around the cladding 12 to provide better protection. To promote hydrogen diffusion into its core, the multimode hydrogen-sensing fiber typically excludes such coatings.

Figure 3:
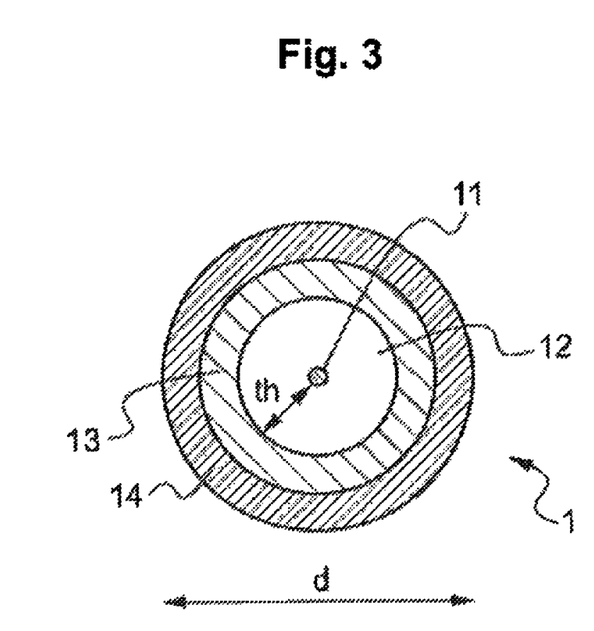
FIG. 3 schematically depicts an exemplary hydrogen-sensing optical fiber according to yet another embodiment of the present invention.

FIG. 3 schematically depicts an exemplary hydrogen-sensing, single-mode optical fiber. This exemplary hydrogen-sensing, single-mode fiber 1 includes a core 11, which might be formed of germanium and/or fluorine doped silica, and a cladding 12, which might be formed from pure silica. As depicted in FIG. 3, the exemplary multimode hydrogen-sensing fiber 1 has a diameter (d) and a cladding thickness (th). A typical outer diameter (d) is between about 30 microns and 150 microns, more typically between about 30 microns and 80 microns. A typical cladding thickness (th) is between about 10 microns and 50 microns, more typically between about 10 microns and 30 microns (e.g., 15-20 microns). As noted and as depicted in FIG. 3, a single-mode hydrogen-sensing fiber typically includes one or more thin fiber coatings (e.g., a primary coating 13 and a secondary coating 14) around the cladding 12 to provide better protection.

To ensure a fast and reliable response to the presence of hydrogen, regardless of environmental changes in the surroundings (e.g., temperature changes), the multimode sensing fiber as depicted in FIG. 2 or the single-mode sensing fiber as depicted in FIG. 3 might possess alkali and metallic impurities in the core and/or cladding of less than 0.1 parts per billion (ppb). That is, the core and/or cladding may be formed from ultra-high purity glass, which has fewer glass defects, to facilitate optical-fiber stability over long periods of time. Likewise, where the multimode sensing fiber as depicted in FIG. 2 or the single-mode sensing fiber as depicted in FIG. 3 employ a glass cladding, the glass cladding might be optionally surrounded by a thin, gas-permeable polymeric coating that is resistant to temperatures in the range of 20° C.-300° C. (e.g., 50° C.-150° C.).

Figure 4:
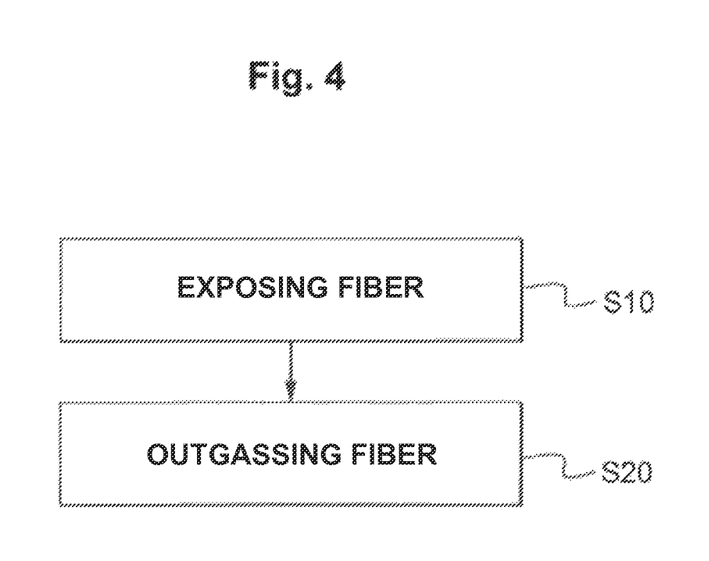
FIG. 4 schematically depicts an exemplary hydrogen-sensing-fiber pretreatment method according to an embodiment of the present invention.

FIG. 4 schematically depicts an exemplary hydrogen-sensing-fiber pretreatment method according to an embodiment of the present invention. In brief, this hydrogen-sensing-fiber pretreatment method includes a step S10 of exposing the sensing fiber to a particular atmosphere and a step S20 of outgassing in another atmosphere. Thereafter, the resulting sensing fiber can be effectively calibrated for hydrogen detection. For instance, the sensing fiber's reversible attenuation can be calibrated against atmospheric hydrogen concentration(s) (e.g., establishing the intensity of the 1240-nanometer peak with respect to hydrogen partial pressure and temperature).

Step S10 includes exposing an optical fiber to an atmosphere having a predetermined hydrogen concentration, under a predetermined pressure, under a predetermined temperature, for a first predetermined time. In this regard, the optical fiber is typically saturated with a hydrogen-rich atmosphere for a period that is sufficient to substantially react the defects in the optical core and/or the cladding with hydrogen. Typically, the predetermined pressure ranges from about 1 to 10 atmospheres, more typically from about 2 to 10 atmospheres. Typically, the predetermined temperature ranges from about 20° C. to 150° C., more typically from about 50° C. to 90° C.

Typically, the first predetermined time ranges from about 30 hours to 1000 hours. The first predetermined time, which is also the treatment duration of the exposing step, is defined by the time after which the pre-existing core defects and/or pre-existing cladding defects have substantially reacted with hydrogen. This time period will be shorter for higher temperature and pressure conditions. In case of hydrogen pretreatment, for example, the time needed to reach defect saturation can be determined by the saturation of SiOH peak at 1385 nanometers.

The step S20 includes outgassing at predetermined conditions (e.g., pressure and temperature to accelerate removal of excess hydrogen). Notably, the temperature is lower or equal to the temperature of optical-fiber pretreatment, typically at ambient conditions for a second predetermined time. Typically, the second predetermined time is at least two weeks. This outgassing step S20 can be advantageously combined with a sensing-fiber storage period.

During hydrogen-sensing-fiber pretreatment, an optical fiber is exposed to a hydrogen-rich environment (e.g., more than 4 weight percent hydrogen, such as about 5-50 weight percent hydrogen or 25-75 weight percent hydrogen) for an extended period, typically at elevated pressure and temperature. In this regard, it is most efficient and fastest to use a predetermined hydrogen concentration that ranges from about 75-100 weight percent, more typically about 90-100 weight percent. This, of course, requires a secured and safe environment to prevent catastrophic explosions. That said, it is within the scope of the present invention to use a predetermined hydrogen concentration of 4 weight percent or less, typically a hydrogen-concentration range between about 1 and 4 weight percent to decrease the risk of explosion.

After making a hydrogen-sensing fiber by passivating defects in an optical fiber, subsequent exposure of the hydrogen-sensing optical fiber to hydrogen gas does not cause further significant irreversible interactions between (i) the defects in the optical core and/or the defects in the cladding and (ii) hydrogen gas.

Figure 5:
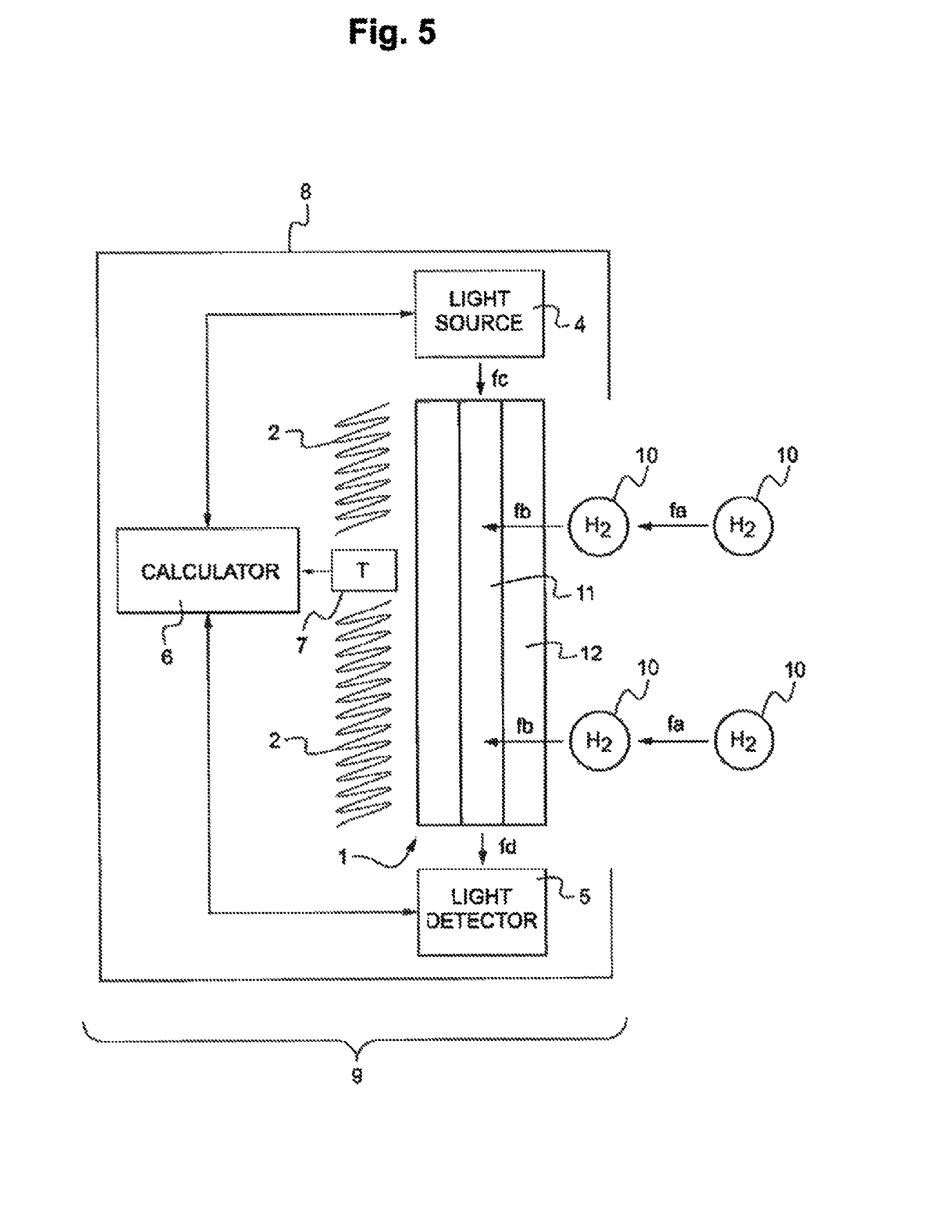
FIG. 5 schematically depicts an exemplary sensor that includes in its casing a hydrogen-sensing optical fiber according to an embodiment of the present invention.

Similarly, after making a hydrogen-sensing fiber by passivating defects in an optical fiber, subsequent exposure of the hydrogen-sensing optical fiber to hydrogen gas does not cause further significant irreversible hydrogen-induced attenuation losses at any wavelength, FIG. 5 schematically depicts an exemplary sensor that includes in its casing a hydrogen-sensing optical fiber according to an embodiment of the invention. In the casing 8 of a hydrogen sensor 9, there are a hydrogen-sensing fiber 1, a heater 2, a light source 4, a light detector 5, a calculator 6, and a temperature sensor 7.

The light source 4 is adapted to launch light into the sensing fiber 1 at a first wavelength (e.g., about 1242 nanometers) where the sensing fiber 1 can undergo reversible hydrogen-induced losses. The light detector 5 is adapted to detect light emitted from the sensing fiber 1 at the same first wavelength (e.g., as launched by the light source 4). The presence of hydrogen in the sensing fiber's optical core 11 will cause reversible attenuation at the first wavelength (e.g., as launched by the light source 4 and detected by the light detector 5).

Outside the sensor 9 and its casing 8, there is the outside environment that includes hydrogen 10. This hydrogen 10 moves from outside the casing 8 into the casing 8. This air circulation is shown by the arrow designated fa. Then, inside the casing 8, there is hydrogen 10, which will diffuse into sensing fiber 1, first through cladding 12 and then into the core 11. This diffusion of hydrogen 10 within the sensing fiber 1 is shown by the arrow designated fb. In this way, the sensing fiber 1 is in contact with the atmosphere outside the hydrogen sensor 9.

The light source 4 (e.g., a broad-spectrum light source or a plurality of light sources emitting at particular wavelengths) launches light into the core 11 at one end of sensing fiber 1. The launched light is shown by the arrow designated fc. This light propagates within the sensing fiber 1 until emerging from the other end of sensing fiber 1. This light, which is shown by the arrow designated fd, is detected by the light detector 5 and thereafter analyzed by the calculator 6 to determine fiber attenuation. Increased fiber attenuation indicates the presence of hydrogen in the core 11, and the degree of increased fiber attenuation yields the calculated hydrogen concentration.

In order to make more precise the measurement of fiber-attenuation increase because of hydrogen presence in the core 11, the first wavelength is chosen within the spectral range of a reversible attenuation peak due to hydrogen presence in the core 11. Typically, the peak in wavelength range corresponding to first overtone of hydrogen resonance frequency is chosen, because this is the highest peak among all overtones, which leads to a more precise computation of fiber-attenuation increase.

Peak of first overtones is preferable to peak of fundamental, because peak of fundamental is at a wavelength of more than 2000 nanometers (i.e., 2 microns), which is not in silica's "transmission window." That is to say, peak of fundamental lies in a spectral range where attenuation is intrinsically very high, so detecting a fiber-attenuation increase would be more difficult and would lead to less precise fiber-attenuation measurement and, in turn, a less precise hydrogen-concentration quantification. Advantageously, first wavelength is about 1242 nanometers (e.g., 1242 nanometers ±2 nanometers) and first overtone peak ranges from 1240 nanometers to 1244 nanometers.

Sensor 9 also includes a heater 2, which is adapted to heat sensing fiber 1. This heater 2 may be disposed around sensing fiber 1. Heating the sensing fiber 1 has a first positive effect on sensor response time, because heating accelerates hydrogen diffusion into the center of the sensing fiber's core 11. Heating the sensing fiber 1, however, has a second negative effect on hydrogen-quantification precision, because it reduces the level of the reversible attenuation peak caused by hydrogen presence in the sensing fiber's core 11. That said, the first positive effect (i.e., faster response time) outweighs the second negative effect (i.e., quantification precision) over a wide temperature range (and significantly outweighs the second negative effect over a narrower temperature range).

The heater 2 is typically adapted to constantly heat the sensing fiber 1 when the sensor 9 is in use. If hydrogen concentration measures are needed only at long time intervals, however, the heater 2 may be configured to intermittently heat the sensing fiber 1 when the sensor 9 is in use.

The sensor 9 also includes a calculator 6, which is adapted to compute fiber attenuation by comparing detected light power to launched light power at the first wavelength (e.g., 1242 nanometers). Calculator 6 is also adapted to quantify, directly or indirectly from calculated fiber attenuation, hydrogen presence in the surrounding outside atmosphere.

To make measurements more accurate in an environment where outside conditions can vary both greatly and quickly, the calculator 6 may be adapted to calculate the difference between fiber attenuation at the first wavelength (e.g., 1242 nanometers) and fiber attenuation at a second wavelength (e.g., 1310 nanometers). In this regard, attenuation within the sensing fiber 1 at the second wavelength is independent of the quantity of hydrogen present in the sensing fiber's core 11. The calculator 6 may be configured to quantify hydrogen presence in the outside atmosphere that surrounds the sensor 9 from this calculated difference in attenuation at the respective wavelengths.

In particular, the calculator 6 calculates attenuation at the first wavelength by comparing the power of the light detected by the light detector 5 with the power of the light launched by the light source 4 and then quantifying atmospheric hydrogen either directly or indirectly from the calculated attenuation at the first wavelength.

Moreover, the calculator 6 is configured for calculating the reversible attenuation at the first wavelength, corrected in view of system-drift attenuation calculated at a second wavelength. In this regard, the presence of hydrogen in the sensing fiber's core 11 will cause neither irreversible nor reversible attenuation at a second wavelength. The calculator 6 is further configured for quantifying atmospheric hydrogen from a calculated difference in attenuation at the first wavelength and the second wavelength.

To make measurements more accurate in an environment where outside conditions can vary both greatly and quickly, the hydrogen sensor 9 may include a temperature sensor 7 that is coupled to both the sensing fiber 1 and the calculator 6 to provide the calculator 6 with the temperature of the sensing fiber 1. The calculator 6 is then configured to correct calculated fiber attenuation(s) according to any temperature variations of the sensing fiber 1. In other words, the temperature sensor 7 is configured for measuring the temperature of the sensing fiber 1 and transmitting a signal to the calculator 6 representing the temperature of the sensing fiber 1, and the calculator 6 is configured for correcting calculated attenuation according to the measured temperature of the sensing fiber 1 (e.g., temperature variations).

Figure 6:
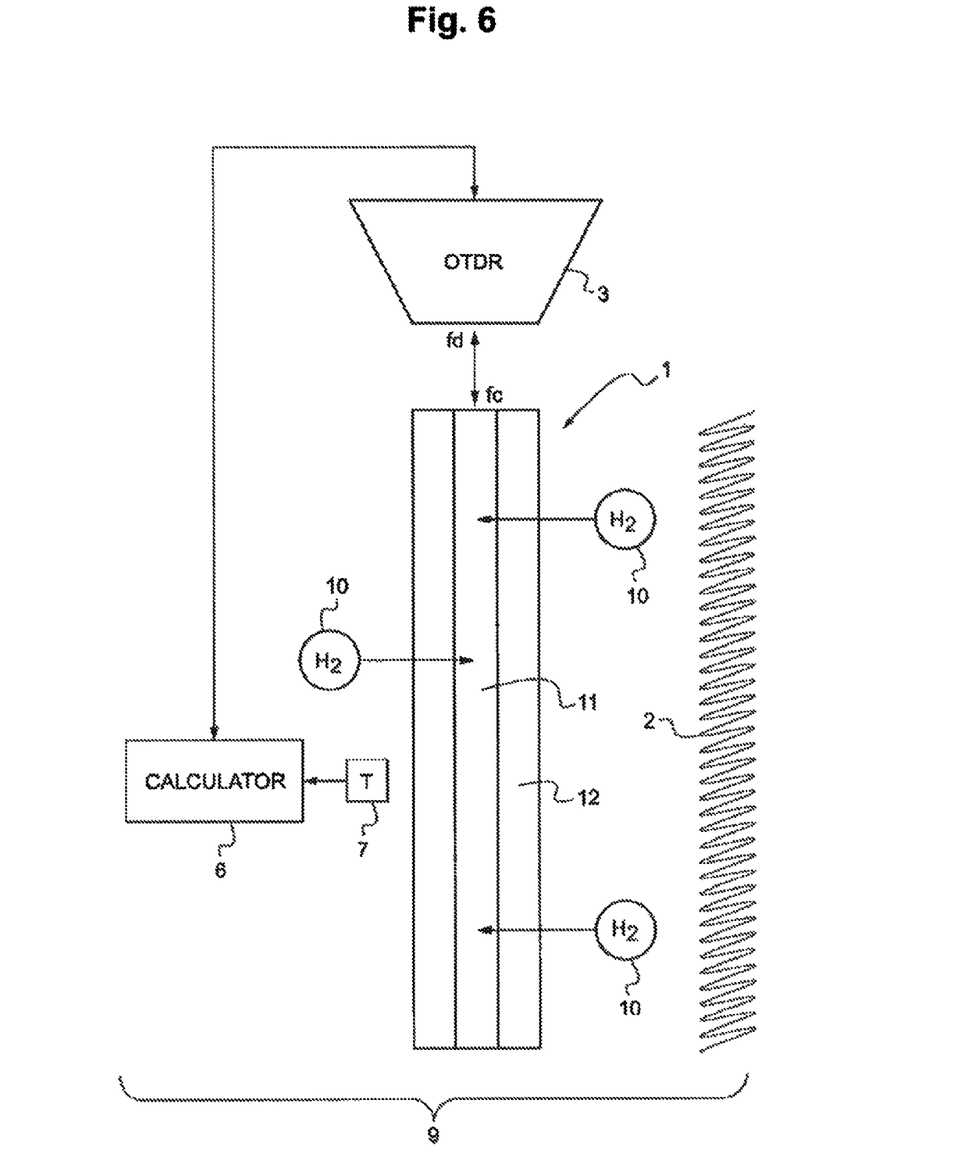
FIG. 6 schematically depicts an exemplary distributed sensor that includes a hydrogen-sensing optical fiber according to an embodiment of the present invention.

FIG. 6 schematically depicts an exemplary distributed sensor that includes a hydrogen-sensing optical fiber according to an embodiment of the present invention. Hydrogen sensor 9 includes a sensing fiber 1, a heater 2, an optical time-domain reflectometer 3 (i.e., an "OTDR"), a calculator 6, and a temperature sensor 7.

The OTDR 3 encompasses a light source 4 and a light detector 5. The light source 4 is adapted to launch light into the sensing fiber 1 at a first wavelength (e.g., about 1242 nanometers) where sensing fiber 1 can still undergo reversible hydrogen-induced losses. The light detector 5 is adapted to detect light emitted from the sensing fiber 1 at the same first wavelength. Hydrogen 10 diffuses into the sensing fiber's core 11 in the same way as discussed with respect to FIG. 5. The presence of hydrogen in the sensing fiber's optical core 11 will cause reversible attenuation at the first wavelength.

In particular, the OTDR 3 launches laser pulses into the core 11 at one end of sensing fiber 1. The launched light is shown by the arrow designated fc. Along the sensing fiber 1, the laser pulses are reflected by Rayleigh scattering. By detecting back scattered laser pulses in the OTDR 3 at the same end where the laser pulses were launched, and by analyzing back scattered laser pulses in the calculator 6, fiber attenuation can be computed (e.g., in the same way as discussed with respect to FIG. 5). Detected light is shown by the arrow designated fd. Increased fiber attenuation indicates the presence of hydrogen in the core 11, and the degree of increased fiber attenuation yields the calculated hydrogen concentration. Moreover, optical time-domain reflectometry can indicate the position of fiber-attenuation increase within the sensing fiber 1, which facilitates identification of the precise location of elevated hydrogen concentration along the sensing fiber 1.

In an exemplary hydrogen sensor 9, the length of sensing fiber 1 is at least 100 meters, typically at least 500 meters, more typically at least 1000 meters. In this way, large areas can be monitored by a distributed hydrogen sensor 9.

Typically, for at least one point along sensing fiber 1, the shorter of the respective distances to the source 4 and the detector 5 is at least 50 meters, more typically at least 200 meters (e.g., at least 500 meters).

In case of an OTDR 3 that encompasses the source 4 and the detector 5, for at least one point along sensing fiber 1, the distance to the OTDR 3 is typically at least 5 meters. Optical time-domain reflectometry usually needs a minimal length of sensing fiber 1 to be precise. In a small hydrogen-detection area, the optical fiber (e.g., a bend-insensitive fiber) may be wound in order to use optical time-domain reflectometry with a high precision with respect to the location of hydrogen in the detection area.

Figure 7:
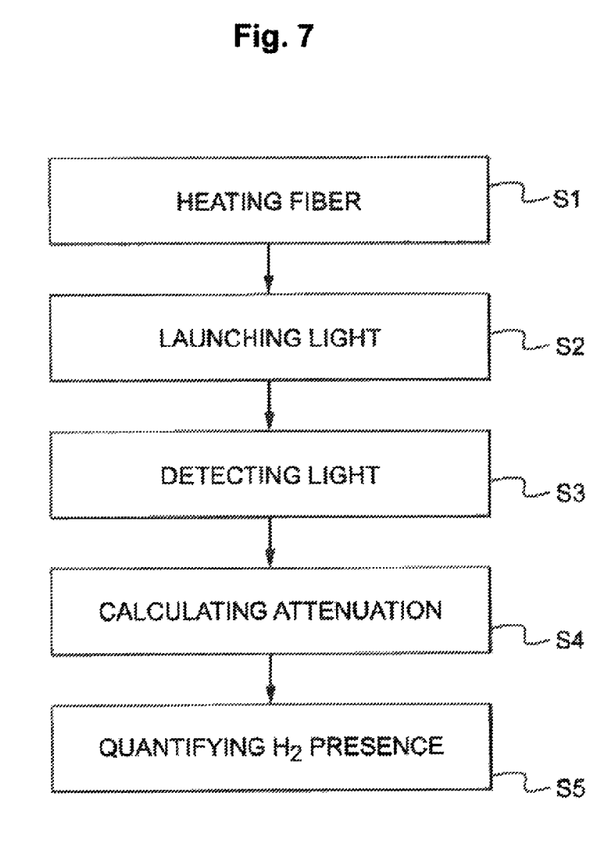
FIG. 7 schematically depicts an exemplary hydrogen-detecting method according to an embodiment of the present invention.

By way of further illustration, FIG. 7 schematically depicts an exemplary hydrogen-detecting method according to an embodiment of the present invention (e.g., a method of detecting and quantifying atmospheric hydrogen). In brief, this hydrogen-detecting method includes a step S1 of heating, a step S2 of launching light, a step S3 of detecting light, a step S4 of calculating attenuation, and a step S5 of quantifying hydrogen presence. The exemplary hydrogen sensors depicted in FIG. 5 and FIG. 6 may be used to detect the presence of hydrogen in accordance with this exemplary method.

Step S1 includes heating the sensing fiber so that its temperature exceeds the temperature of the outside atmosphere surrounding the hydrogen sensor by at least 10° C., typically by at least 20° C. In practice, to keep the sensing fiber temperature constant, the heating set point is chosen so as to maintain the sensing fiber's temperature above that maximum possible outside atmospheric temperature by at least 10° C. (e.g., by 20° C. or more). This facilitates hydrogen detection that is independent from temperature variations in the external environment.

The sensing response time is further reduced by associating a thin optical-fiber cladding and a controlled heated temperature between 20° C. and 300° C., more typically between 50° C.-150° C. Heating the sensing fiber to a constant temperature that is, for example, at least 20° C. higher than the maximum temperature that would otherwise be experienced by the sensing fiber ensures sensing reliability regardless of variations in the outside environment temperature.

The intensity of the heating step S1 is selected so that a hydrogen concentration of 1 percent or more in the outside atmosphere (i.e., surrounding the hydrogen sensor) can be detected and quantified in less than 1 hour (e.g., less than 10 minutes). This is much faster response than other systems for detecting the mere presence of hydrogen, much less quantifying hydrogen concentration. By way of contrast, the hydrogen-detection response for other systems could range from at least several hours to several days.

With reference to FIG. 7, step S2 includes launching light at a first wavelength into the hydrogen-sensing optical fiber. At this first wavelength, the presence of hydrogen in the hydrogen-sensing optical fiber's optical core will cause reversible attenuation. Step S3 includes detecting light emerging from the sensing fiber at the first wavelength. Step S4 includes calculating attenuation at the first wavelength by comparing the detected light power at the first wavelength to launched light power at the first wavelength. Step S5 includes quantifying, directly or indirectly from calculated fiber attenuation, hydrogen presence in the surrounding outside atmosphere.

In many harsh and hazardous environments (e.g., storage of radioactive waste), gas detection is required for several years to several decades. Using the sensing fiber of the present invention provides rapid and reliable hydrogen detection over several decades yet requires minimal maintenance. Moreover, the sensing fiber of the present invention is useful in both distributed sensing systems (e.g., detecting the presence of hydrogen along the optical fiber to help locate hydrogen leaks) and deported sensing systems (e.g., analyzing the measurements remotely from the hydrogen sensor).

Figure 8:
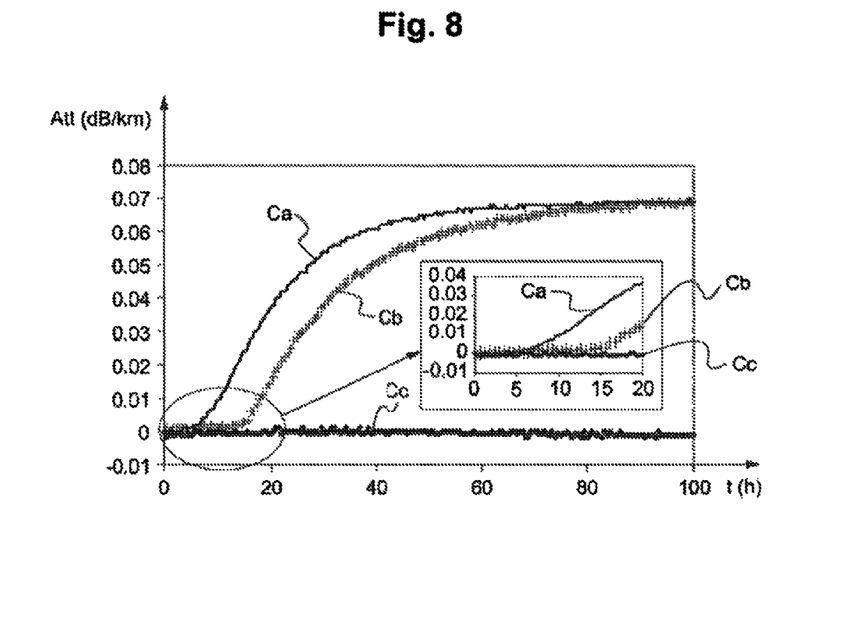
FIG. 8 graphically depicts increases in optical-fiber attenuation as a function of time because of hydrogen diffusion in the optical-fiber core in different conditions.

FIG. 8 graphically depicts increases in optical-fiber attenuation (Att) as a function of time in hours (t(h)) because of hydrogen diffusion in the optical-fiber core in different conditions. Curve Ca represents attenuation peak variation for an exemplary sensing fiber according to an embodiment of the invention. Curve Cb represents attenuation peak variation for a sensing fiber according to an optical fiber without hydrogen pretreatment. Curve Cc represents attenuation peak variation (i.e., low variation) for a reference optical fiber at 1310 nanometers, hereinafter referred to as the "baseline."

FIG. 8 illustrates 1242-nanometer peak variation, which indicates the presence of molecular hydrogen in the core. FIG. 8 illustrates the effects of hydrogen pretreatment on delay time detection of hydrogen at 1242 nanometers for a standard 125-micron-diameter glass cladding (e.g., a single-mode fiber with a 10-micron core and a 57.5-thick glass cladding). These measurements were performed for 144 hours under 1-percent hydrogen concentration at 1 atmosphere and at 70° C. Hydrogen presence in the atmosphere surrounding the sensing fiber is detected via the measurement of a specific peak growth that is related to molecular hydrogen $H_2$. This peak spectrally ranges from about 1240 nanometers to about 1244 nanometers, corrected with a baseline that is determined from a specific wavelength in the optical-fiber-attenuation spectrum (e.g., at 1310 nanometers, where irreversible OH—peak has already been saturated by the sensing fiber's hydrogen pretreatment). The baseline is unaffected by the presence of hydrogen. As illustrated by FIG. 8, the exemplary sensing fiber according to the present invention provides a shorter response time for hydrogen detection.

Figure 9:
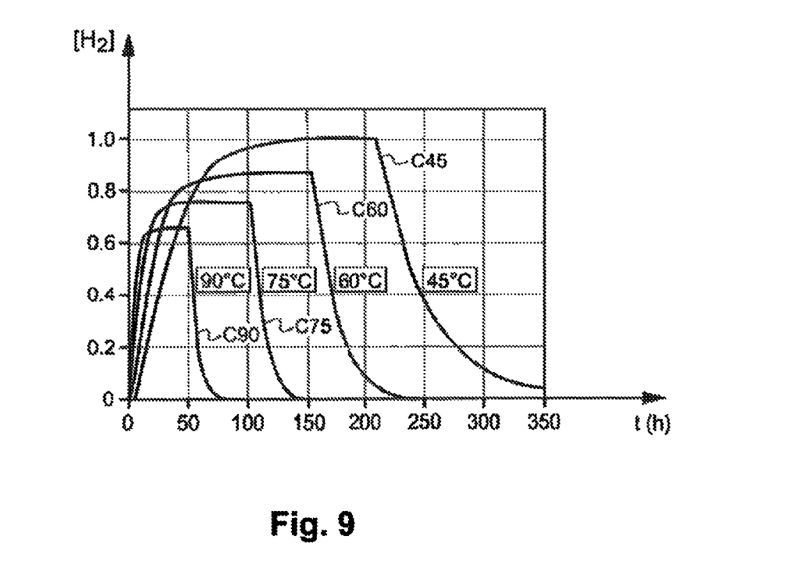
FIG. 9 graphically depicts hydrogen-presence detection as a function of time because of hydrogen diffusion in the optical-fiber core for different hydrogen-sensing-fiber temperatures.

FIG. 9 graphically depicts hydrogen detection ($H_2$) (expressed in a normalized, relative way) as a function of time in hours (t(h)) because of hydrogen diffusion in the optical-fiber core for different hydrogen-sensing-fiber temperatures. Curve C90 represents hydrogen detection as a function of time for a sensing-fiber temperature of 90° C. Curve C75 represents hydrogen detection as a function of time for a sensing-fiber temperature of 75° C. Curve C60 represents hydrogen detection as a function of time for a sensing-fiber temperature of 60° C. Curve C45 represents hydrogen detection as a function of time for a sensing-fiber temperature of 45° C.

FIG. 9 illustrates the effects of temperature on the time needed for hydrogen to reach the core of a sensing fiber having a standard 125-micron-diameter glass cladding (e.g., a single-mode fiber with a 10-micron core and a 57.5-thick glass cladding). The respective detection levels quickly increase until being stabilized; thereafter, detection levels decrease because of the disappearance of hydrogen via outgassing.

As illustrated by FIG. 9, the higher the sensing-fiber temperature, the quicker the detection and the shorter the sensing-fiber response time. The higher the sensing-fiber temperature, however, the smaller the increase in peak attenuation and the less precise the hydrogen quantification. The former, positive effect is more pronounced than is the latter, negative effect.

Figure 10:
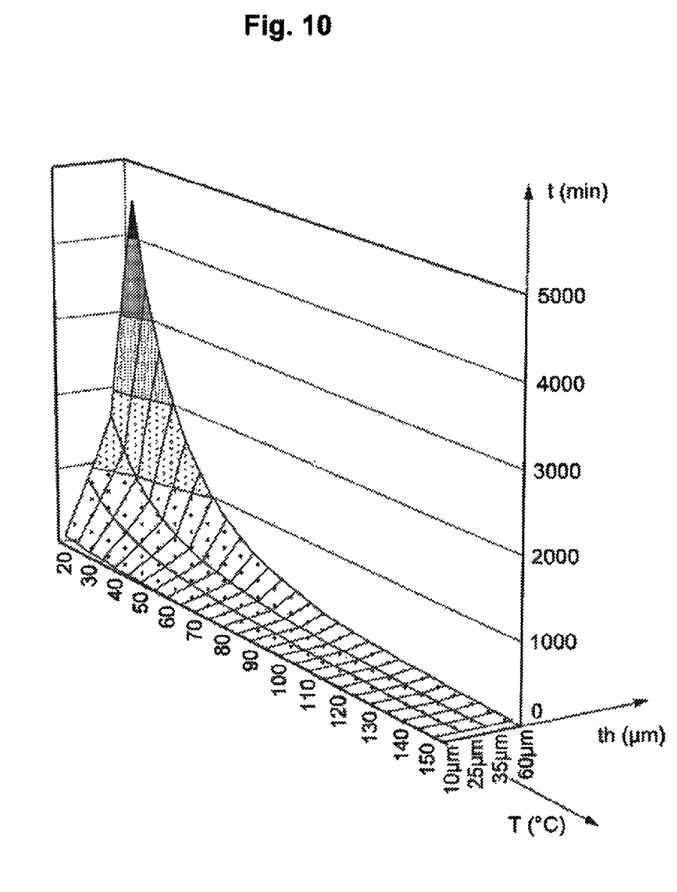
FIG. 10 graphically depicts hydrogen diffusion time in the optical-fiber core as a function of both hydrogen-sensing-fiber temperature and hydrogen-sensing-fiber cladding thickness.

FIG. 10 graphically depicts hydrogen diffusion time (t(min)) in an exemplary optical-fiber core as a function of both hydrogen-sensing-fiber temperature and hydrogen-sensing-fiber cladding thickness in microns. FIG. 10 illustrates the potential for reducing detection time delays by reducing the sensing fiber's glass cladding thickness and increasing the sensing fiber's temperature. In this regard, a response time as low as several tens of minutes (e.g., 20-30 minutes) is achievable. Moreover, the response time could be significantly reduced by replacing the glass cladding with a polymeric cladding.

EXAMPLE

In accordance with the present invention, an exemplary hydrogen-sensing fiber having an 80-micron-diameter plastic cladding may be manufactured as follows:

First, a core rod is manufactured. A step-index profile without clad layers is realized by Plasma Chemical Vapor Deposition (PCVD) technology by successive deposition of doped layers of germanium and/or fluorine onto the inner surface of a substrate tube. In this regard, the co-doping using germanium and fluorine facilitates the achievement of a core refractive index that is equivalent to that of pure silica (e.g., 1.457). Second, the core rod is collapsed. Third, the substrate tube is removed by successive steps of machining and HF etching.

Fourth, the resulting core rod is drawn to a 50-micron-diameter core. To achieve reduced glass defects in the core, the optical fiber may be drawn at low drawing speeds and low drawing tensions. During drawing, the core is coated in line with a low-index polymer to a coating thickness of 15 microns. With respect to the plastic coating, an appropriate polymer index (e.g., 1.36-1.46) permits the achievement of an adequate numerical aperture. A plastic coating with a cladding index in the range of 1.36-1.46 (at 850 nanometers) is possible using commercially available resins.

Fifth, the resulting optical fiber is treated in an autoclave for 72 hours under a pressure of 10 atmospheres of pure molecular hydrogen at 75° C. This pretreatment step saturates substantially all, if not all, glass defects. Sixth, the high-pressure hydrogen in the autoclave is replaced by nitrogen ($N_2$), and then the optical fiber is outgassed for one week under atmospheric pressure at 20° C. (i.e., STP). Thereafter, the optical fiber is stored at room temperature in an ambient atmosphere (i.e., room-temperature air) for at least two more weeks to complete the outgassing of the molecular hydrogen.

The resulting sensing fiber can thereafter be incorporated into hydrogen sensor, such as a cable structure of a durable sensor system that permits continuous heating of the sensing fiber to a temperature that is at least 20° C. above the maximum possible environment temperature (i.e., to overcome temperature variations in the external environment). As will be understood by those having ordinary skill in the art, the cable structure that incorporates the sensing fiber permits hydrogen gas surrounding the sensor system to have direct contact with the sensing fiber.

This exemplary sensing fiber can reliably measure molecular hydrogen concentration in the environment by measuring the specific and reversible peak near at a wavelength of about 1242 nanometers (e.g., between about 1240 nanometers and 1244 nanometers). The sensing fiber provides a short response delay by facilitating hydrogen-diffusion toward the sensing fiber's core. The detection response can be less than one minute at a sensing-fiber temperature of 50° C. and less than 30 seconds at a sensing-fiber temperature of 65° C. Moreover, the relationship between hydrogen content and reversible, hydrogen-induced losses (HIL) at a wavelength near 1242 nanometers will remain predictable over time (e.g., several decades).

To supplement the present disclosure, this application incorporates entirely by reference the following U.S. patents and U.S. patent application publications: U.S. Pat. No. 5,153,931 for Fiber Optic Hydrogen Sensor; U.S. Pat. No. 5,783,152 for Hydrogen Gas and Temperature Fiber Optic Sensor System; U.S. Patent Application Publication No. 2004/0047576 for Optical Fiber and Evaluation Method Thereof; U.S. Patent Application Publication No. 2005/0118064 for Sensor System and Method; U.S. Patent Application Publication No. 2009/0129721 for Fiber Optic Gas Sensor; U.S. Patent Application Publication No. 2011/0199604 for Optical Fiber Hydrogen Detection System and Method; and U.S. Patent Publication No. 2011/0228275 for Fiber Optic Hydrogen Purity Sensor and System.

To supplement the present disclosure, this application incorporates entirely by reference the following commonly assigned patents, patent application publications, and patent applications: U.S. Pat. No. 4,838,643 for a Single Mode Bend Insensitive Fiber for Use in Fiber Optic Guidance Applications (Hodges et al.); U.S. Pat. No. 7,623,747 for a Single Mode Optical Fiber (de Montmorillon et al.); U.S. Pat. No. 7,587,111 for a Single-Mode Optical Fiber (de Montmorillon et al.); U.S. Pat. No. 7,356,234 for a Chromatic Dispersion Compensating Fiber (de Montmorillon et al.); U.S. Pat. No. 7,483,613 for a Chromatic Dispersion Compensating Fiber (Bigot-Astruc et al.); U.S. Pat. No. 7,526,177 for a Fluorine-Doped Optical Fiber (Matthijsse et al.); U.S. Pat. No. 7,555,186 for an Optical Fiber (Flammer et al.); U.S. Pat. No. 8,055,111 for a Dispersion-Shifted Optical Fiber (Sillard et al.); U.S. Pat. No. 8,041,172 for a Transmission Optical Fiber Having Large Effective Area (Sillard et al.); International Patent Application Publication No. WO 2009/062131 A1 for a Microbend-Resistant Optical Fiber (Overton); U.S. Pat. No. 8,265,442 for a Microbend-Resistant Optical Fiber (Overton); U.S. Pat. No. 8,145,025 for a Single-Mode Optical Fiber Having Reduced Bending Losses (de Montmorillon et al.); U.S. Pat. No. 7,889,960 for a Bend-Insensitive Single-Mode Optical Fiber (de Montmorillon et al.); U.S. Patent Application Publication No. US2010/0021170 A1 for a Wavelength Multiplexed Optical System with Multimode Optical Fibers (Lumineau et al.); U.S. Pat. No. 7,995,888 for a Multimode Optical Fibers (Gholami et al.); U.S. Patent Application Publication No. US2010/0119202 A1 for a Reduced-Diameter Optical Fiber (Overton); U.S. Patent Application Publication No. US2010/0142969 A1 for a Multimode Optical System (Gholami et al.); U.S. Pat. No. 8,259,389 for an Amplifying Optical Fiber and Method of Manufacturing (Pastouret et al.); U.S. Patent Application Publication No. US2010/0135627 A1 for an Amplifying Optical Fiber and Production Method (Pastouret et al.); U.S. Patent Application Publication No. US2010/0142033 for an Ionizing Radiation-Resistant Optical Fiber Amplifier (Regnier et al.); U.S. Pat. No. 8,274,647 for a Method of Classifying a Graded-Index Multimode Optical Fiber (Gholami et al.); U.S. Patent Application Publication No. US2010/0189397 A1 for a Single-Mode Optical Fiber (Richard et al.); U.S. Pat. No. 8,290,324 for a Single-Mode Optical Fiber Having an Enlarged Effective Area (Sillard et al.); U.S. Pat. No. 8,301,000 for a Single-Mode Optical Fiber (Sillard et al.); U.S. Patent Application Publication No. US2010/0214649 A1 for an Optical Fiber Amplifier Having Nanostructures (Burov et al.); U.S. Pat. No. 8,009,950 for a Multimode Fiber (Molin et al.); U.S. Patent Application Publication No. US2010/0310218 A1 for a Large Bandwidth Multimode Optical Fiber Having a Reduced Cladding Effect (Molin et al.); U.S. Patent Application Publication No. US2011/0058781 A1 for a Multimode Optical Fiber Having Improved Bending Losses (Molin et al.); U.S. Patent Application Publication No. US2011/0064367 A1 for a Multimode Optical Fiber (Molin et al.); U.S. Patent Application Publication No. US2011/0069724 A1 for an Optical Fiber for Sum-Frequency Generation (Richard et al.); U.S. Patent Application Publication No. US2011/0116160 A1 for a Rare-Earth-Doped Optical Fiber Having Small Numerical Aperture (Boivin et al.); U.S. Pat. No. 8,280,213 for a High-Bandwidth, Multimode Optical Fiber with Reduced Cladding Effect (Molin et al.); U.S. Patent Application Publication No. US2011/0123162 A1 for a High-Bandwidth, Dual-Trench-Assisted Multimode Optical Fiber (Molin et al.); U.S. Patent Application Publication No. US2011/0135262 A1 for a Multimode Optical Fiber with Low Bending Losses and Reduced Cladding Effect (Molin et al.); U.S. Patent Application Publication No. US2011/0135263 A1 for a High-Bandwidth Multimode Optical Fiber Having Reduced Bending Losses (Molin et al.); U.S. Patent Application Publication No. US2011/0188826 A1 for a Non-Zero Dispersion Shifted Optical Fiber Having a Large Effective Area (Sillard et al.); U.S. Patent Application Publication No. US2011/0188823 A1 for a Non-Zero Dispersion Shifted Optical Fiber Having a Short Cutoff Wavelength (Sillard et al.); U.S. Patent Application Publication No. 2011/0217012 A1 for a Broad-Bandwidth Multimode Optical Fiber Having Reduced Bending Losses (Bigot-Astruc et al.); U.S. Patent Application Publication No. 2011/0229101 A1 for a Single-Mode Optical Fiber (de Montmorillon et al.); U.S. Patent Application Publication No. 2012/0051703 A1 for a Single-Mode Optical Fiber (Bigot-Astruc et al.); U.S. Patent Application Publication No. 2012/0040184 A1 for a Method of Fabricating an Optical Fiber Preform (de Montmorillon et al.); U.S. Patent Application Publication No. 2012/0092651 A1 for a Multimode Optical Fiber Insensitive to Bending Losses (Molin et al.); U.S. Patent Application Publication No. 2012/0134376 A1 for a Radiation-Insensitive Optical Fiber Doped with Rare Earths (Burov et al.); U.S. Patent Application Publication No. 2012/0148206 A1 for a Rare-Earth-Doped Optical Fiber (Boivin et al.); U.S. Patent Application Publication No. 2012/0195549 A1 for a Broad-Bandwidth Optical Fiber (Molin et al.); U.S. Patent Application Publication No. 2012/0195561 A1 for a Multimode Optical Fiber (Molin et al.); U.S. Patent Application Publication No. 2012/00224254 A1 for a Rare-Earth-Doped Amplifying Optical Fiber (Burov et al.); U.S. Patent Application Publication No. 2012/0243843 A1 for a Bend-Resistant Multimode Optical Fiber, (Molin et al.); U.S. Patent Application Publication No. 2012/0251062 A1 for a Multimode Optical Fiber, (Molin et al.); U.S. patent application Ser. No. 13/456,562 for a High-Bandwidth, Radiation-Resistant Multimode Optical Fiber, filed Apr. 26, 2012, (Krabshuis et al.); U.S. patent application Ser. No. 13/481,150 for a Single-Mode Optical Fiber, filed May 25, 2012, (Sillard et al.); U.S. patent application Ser. No. 13/491,953 for a Single-Mode Optical Fiber, filed Jun. 8, 2012, (Sillard et al.) U.S. patent application Ser. No. 13/534,793 for a Multimode Optical Fiber, filed Jun. 27, 2012, (Bigot-Astruc et al.); and U.S. patent application Ser. No. 13/627,351 for a Trench-Assisted Multimode Optical Fiber, filed Sep. 26, 2012, (Molin).

To supplement the present disclosure, this application further incorporates entirely by reference the following commonly assigned patents, patent application publications, and patent applications: U.S. Pat. No. 5,574,816 for Polypropylene-Polyethylene Copolymer Buffer Tubes for Optical Fiber Cables and Method for Making the Same; U.S. Pat. No. 5,717,805 for Stress Concentrations in an Optical Fiber Ribbon to Facilitate Separation of Ribbon Matrix Material; U.S. Pat. No. 5,761,362 for Polypropylene-Polyethylene Copolymer Buffer Tubes for Optical Fiber Cables and Method for Making the Same; U.S. Pat. No. 5,911,023 for Polyolefin Materials Suitable for Optical Fiber Cable Components; U.S. Pat. No. 5,982,968 for Stress Concentrations in an Optical Fiber Ribbon to Facilitate Separation of Ribbon Matrix Material; U.S. Pat. No. 6,035,087 for an Optical Unit for Fiber Optic Cables; U.S. Pat. No. 6,066,397 for Polypropylene Filler Rods for Optical Fiber Communications Cables; U.S. Pat. No. 6,175,677 for an Optical Fiber Multi-Ribbon and Method for Making the Same; U.S. Pat. No. 6,085,009 for Water Blocking Gels Compatible with Polyolefin Optical Fiber Cable Buffer Tubes and Cables Made Therewith; U.S. Pat. No. 6,215,931 for Flexible Thermoplastic Polyolefin Elastomers for Buffering Transmission Elements in a Telecommunications Cable; U.S. Pat. No. 6,134,363 for a Method for Accessing Optical Fibers in the Midspan Region of an Optical Fiber Cable; U.S. Pat. No. 6,381,390 for a Color-Coded Optical Fiber Ribbon and Die for Making the Same; U.S. Pat. No. 6,181,857 for a Method for Accessing Optical Fibers Contained in a Sheath; U.S. Pat. No. 6,314,224 for a Thick-Walled Cable Jacket with Non-Circular Cavity Cross Section; U.S. Pat. No. 6,334,016 for an Optical Fiber Ribbon Matrix Material Having Optimal Handling Characteristics; U.S. Pat. No. 6,321,012 for an Optical Fiber Having Water Swellable Material for Identifying Grouping of Fiber Groups; U.S. Pat. No. 6,321,014 for a Method for Manufacturing Optical Fiber Ribbon; U.S. Pat. No. 6,210,802 for Polypropylene Filler Rods for Optical Fiber Communications Cables; U.S. Pat. No. 6,493,491 for an Optical Drop Cable for Aerial Installation; U.S. Pat. No. 7,346,244 for a Coated Central Strength Member for Fiber Optic Cables with Reduced Shrinkage; U.S. Pat. No. 6,658,184 for a Protective Skin for Optical Fibers; U.S. Pat. No. 6,603,908 for a Buffer Tube that Results in Easy Access to and Low Attenuation of Fibers Disposed Within Buffer Tube; U.S. Pat. No. 7,045,010 for an Applicator for High-Speed Gel Buffering of Flextube Optical Fiber Bundles; U.S. Pat. No. 6,749,446 for an Optical Fiber Cable with Cushion Members Protecting Optical Fiber Ribbon Stack; U.S. Pat. No. 6,922,515 for a Method and Apparatus to Reduce Variation of Excess Fiber Length in Buffer Tubes of Fiber Optic Cables; U.S. Pat. No. 6,618,538 for a Method and Apparatus to Reduce Variation of Excess Fiber Length in Buffer Tubes of Fiber Optic Cables; U.S. Pat. No. 7,322,122 for a Method and Apparatus for Curing a Fiber Having at Least Two Fiber Coating Curing Stages; U.S. Pat. No. 6,912,347 for an Optimized Fiber Optic Cable Suitable for Microduct Blown Installation; U.S. Pat. No. 6,941,049 for a Fiber Optic Cable Having No Rigid Strength Members and a Reduced Coefficient of Thermal Expansion; U.S. Pat. No. 7,162,128 for Use of Buffer Tube Coupling Coil to Prevent Fiber Retraction; U.S. Pat. No. 7,515,795 for a Water-Swellable Tape, Adhesive-Backed for Coupling When Used Inside a Buffer Tube (Overton et al.); U.S. Patent Application Publication No. 2008/0292262 for a Grease-Free Buffer Optical Fiber Buffer Tube Construction Utilizing a Water- Swellable, Texturized Yarn (Overton et al.); European Patent Application Publication No. 1,921,478 A1, for a Telecommunication Optical Fiber Cable (Tatat et al.); U.S. Pat. No. 7,702,204 for a Method for Manufacturing an Optical Fiber Preform (Gonnet et al.); U.S. Pat. No. 7,570,852 for an Optical Fiber Cable Suited for Blown Installation or Pushing Installation in Microducts of Small Diameter (Nothofer et al.); U.S. Pat. No. 7,646,954 for an Optical Fiber Telecommunications Cable (Tatat); U.S. Pat. No. 7,599,589 for a Gel-Free Buffer Tube with Adhesively Coupled Optical Element (Overton et al.); U.S. Pat. No. 7,567,739 for a Fiber Optic Cable Having a Water-Swellable Element (Overton); U.S. Pat. No. 7,817,891 for a Method for Accessing Optical Fibers within a Telecommunication Cable (Lavenne et al.); U.S. Pat. No. 7,639,915 for an Optical Fiber Cable Having a Deformable Coupling Element (Parris et al.); U.S. Pat. No. 7,646,952 for an Optical Fiber Cable Having Raised Coupling Supports (Parris); U.S. Pat. No. 7,724,998 for a Coupling Composition for Optical Fiber Cables (Parris et al.); U.S. Patent Application Publication No. US2009/0214167 A1 for a Buffer Tube with Hollow Channels (Lookadoo et al.); U.S. Patent Application Publication No. US2009/0297107 A1 for an Optical Fiber Telecommunication Cable (Tatat); U.S. Pat. No. 8,195,018 for a Buffer Tube with Adhesively Coupled Optical Fibers and/or Water-Swellable Element; U.S. Patent Application Publication No. US2010/0092135 A1 for an Optical Fiber Cable Assembly (Barker et al.); U.S. Pat. No. 7,974,507 A1 for a High-Fiber-Density Optical Fiber Cable (Louie et al.); U.S. Pat. No. 7,970,247 for a Buffer Tubes for Mid-Span Storage (Barker); U.S. Pat. No. 8,081,853 for Single-Fiber Drop Cables for MDU Deployments (Overton); U.S. Pat. No. 8,041,167 for an Optical-Fiber Loose Tube Cables (Overton); U.S. Pat. No. 8,145,026 for a Reduced-Size Flat Drop Cable (Overton et al.); U.S. Pat. No. 8,165,439 for ADSS Cables with High-Performance Optical Fiber (Overton); U.S. Pat. No. 8,041,168 for Reduced-Diameter Ribbon Cables with High-Performance Optical Fiber (Overton); U.S. Pat. No. 8,031,997 for a Reduced-Diameter, Easy-Access Loose Tube Cable (Overton); U.S. Patent Application Publication No. US2010/0150505 A1 for a Buffered Optical Fiber (Testu et al.); U.S. Patent Application Publication No. US2010/0154479 A1 for a Method and Device for Manufacturing an Optical Preform (Milicevic et al.); U.S. Patent Application Publication No. US2010/0166375 for a Perforated Water-Blocking Element (Parris); U.S. Patent Application Publication No. US2010/0183821 A1 for a UVLED Apparatus for Curing Glass-Fiber Coatings (Hartsuiker et al.); U.S. Patent Application Publication No. US2010/0202741 A1 for a Central-Tube Cable with High-Conductivity Conductors Encapsulated with High-Dielectric-Strength Insulation (Ryan et al.); U.S. Patent Application Publication No. US2010/0215328 A1 for a Cable Having Lubricated, Extractable Elements (Tatat et al.); U.S. Patent Application Publication No. US2011/0026889 A1 for a Tight-Buffered Optical Fiber Unit Having Improved Accessibility (Risch et al.); U.S. Patent Application Publication No. US2011/0064371 A1 for Methods and Devices for Cable Insertion into Latched Conduit (Leatherman et al.); U.S. Patent Application Publication No. 2011/0069932 A1 for a High-Fiber-Density Optical-Fiber Cable (Overton et al.); U.S. Patent Application Publication No. 2011/0091171 A1 for an Optical-Fiber Cable Having High Fiber Count and High Fiber Density (Tatat et al.); U.S. Patent Application Publication No. 2011/0176782 A1 for a Water-Soluble Water-Blocking Element (Parris); U.S. Patent Application Publication No. 2011/0268400 A1 for a Data-Center Cable (Louie et al.); U.S. Patent Application Publication No. 2011/0268398 A1 for a Bundled Fiber Optic Cables (Quinn et al.); U.S. Patent Application Publication No. 2011/0287195 A1 for a Curing Apparatus Employing Angled UVLEDs (Molin); U.S. Patent Application Publication No. 2012/0009358 for a Curing Apparatus Having UV Sources That Emit Differing Ranges of UV Radiation (Gharbi et al.); U.S. Patent Application Publication No. 2012/0014652 A1 for a Adhesively Coupled Optical Fibers and Enclosing Tape (Parris); U.S. Patent Application Publication No. 2012/0040105 A1 for a Method and Apparatus Providing Increased UVLED Intensity (Overton); U.S. Patent Application Publication No. 2012/0057833 A1 for an Optical-Fiber Module Having Improved Accessibility (Tatat); and U.S. Patent Application Publication No. 2012/0213483 A1 for a Optical-Fiber Interconnect Cable (Risch et al.).

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A hydrogen-sensing optical fiber, comprising:
    an optical core that is pure silica or fluorine-doped silica; and
    a cladding surrounding the optical core;
    wherein the defects in the optical core are substantially hydrogen-passivated such that exposing the hydrogen-sensing optical fiber to hydrogen gas does not cause further significant irreversible interactions between the defects in the optical core and hydrogen gas; and
    wherein, at any wavelength of light propagating within the hydrogen-sensing optical fiber, the hydrogen-sensing optical fiber does not exhibit significant irreversible hydrogen-induced attenuation losses after exposure to a hydrogen-rich atmosphere.

2. The hydrogen-sensing optical fiber according to claim 1, wherein the defects in the cladding are substantially hydrogen-passivated such that exposing the hydrogen-sensing optical fiber to hydrogen gas does not cause further significant irreversible interactions between defects in the cladding and hydrogen gas.

3. The hydrogen-sensing optical fiber according to claim 1, wherein the cladding is polymeric.

4. The hydrogen-sensing optical fiber according to claim 1, wherein the cladding has a thickness of between about 5 microns and 60 microns.

5. The hydrogen-sensing optical fiber according to claim 1, wherein the cladding has a thickness of between about 10 microns and 30 microns.

6. The hydrogen-sensing optical fiber according to claim 1, wherein the optical fiber is a multimode fiber.

7. A hydrogen sensor for detecting atmospheric hydrogen, comprising:
    hydrogen-sensing optical fiber according to claim 1;
    a light source for launching light into the hydrogen-sensing optical fiber at a first wavelength;
    a light detector for detecting light at the first wavelength; and
    a heater for heating the hydrogen-sensing fiber;
    wherein, the presence of hydrogen in the hydrogen-sensing optical fiber's optical core will cause reversible attenuation at the first wavelength.

8. The hydrogen sensor according to claim 7, wherein the light source and the light detector are components of an optical time-domain reflectometer.

9. The hydrogen sensor according to claim 7, wherein the first wavelength is about 1242 nanometers.

10. The hydrogen sensor according to claim 7, comprising a calculator configured for calculating attenuation at the first wavelength by (i) comparing the power of the light detected by the light detector with the power of the light launched by the light source and (ii) quantifying atmospheric hydrogen either directly or indirectly from the calculated attenuation at the first wavelength.

11. The hydrogen sensor according to claim 10, wherein:
the presence of hydrogen in the hydrogen-sensing optical fiber's optical core will cause neither irreversible nor reversible attenuation at a second wavelength; and
the calculator is configured for (i) calculating the reversible attenuation at the first wavelength, corrected for system-drift attenuation calculated at a second wavelength, and (ii) quantifying atmospheric hydrogen from a calculated difference in attenuation at the first wavelength and the second wavelength.

12. The hydrogen sensor according to claim 10, comprising:
a temperature sensor that is coupled to the hydrogen-sensing fiber;
wherein the temperature sensor is configured for measuring the temperature of the hydrogen-sensing fiber and transmitting to the calculator the temperature of the hydrogen-sensing fiber; and
wherein the calculator is configured for correcting calculated attenuation according to the measured temperature of the hydrogen-sensing fiber.

13. A method of detecting and quantifying atmospheric hydrogen, comprising:
providing a hydrogen-sensing optical fiber, including (i) an optical core that is pure silica or fluorine-doped silica, and (ii) a cladding surrounding the optical core, wherein the defects in the optical core are substantially hydrogen-passivated such that exposing the hydrogen-sensing optical fiber to hydrogen gas does not cause further significant irreversible interactions between the defects in the optical core and hydrogen gas, and wherein, at any wavelength of light propagating within the hydrogen-sensing optical fiber, the hydrogen-sensing optical fiber does not exhibit significant irreversible hydrogen-induced attenuation losses after exposure to a hydrogen-rich atmosphere;
launching light at a first wavelength into the hydrogen-sensing optical fiber, wherein, the presence of hydrogen in the hydrogen-sensing optical fiber's optical core will cause reversible attenuation at the first wavelength;
detecting light at the first wavelength as emitted from the hydrogen-sensing optical fiber;
calculating attenuation at the first wavelength by comparing detected light power to launched light power; and
quantifying atmospheric hydrogen in the atmosphere surrounding the hydrogen-sensing optical fiber either directly or indirectly from the calculated attenuation at the first wavelength.

14. The method of detecting hydrogen according to claim 13, comprising heating the hydrogen-sensing optical fiber so that the temperature of the hydrogen-sensing optical fiber exceeds by at least 10° C. the temperature of the atmosphere surrounding the hydrogen-sensing optical fiber.

15. The method of detecting hydrogen according to claim 13, comprising detecting and quantifying atmospheric hydrogen in less than one hour in an atmosphere having a hydrogen concentration of 1 weight percent or more.

16. The method of detecting hydrogen according to claim 13, wherein the atmosphere surrounding the hydrogen-sensing optical fiber is radioactive.

17. The hydrogen-sensing optical fiber according to claim 1, wherein, for light propagating within the hydrogen-sensing optical fiber at a wavelength of 1240 nanometers or greater, the hydrogen-sensing optical fiber does not exhibit significant irreversible hydrogen-induced attenuation losses after exposure to a hydrogen-rich atmosphere.

18. The hydrogen-sensing optical fiber according to claim 1, wherein, for light propagating within the hydrogen-sensing optical fiber at any wavelength between 1240 nanometers and 1244 nanometers inclusively, the hydrogen-sensing optical fiber does not exhibit significant irreversible hydrogen-induced attenuation losses after exposure to a hydrogen-rich atmosphere.

19. The hydrogen sensor according to claim 7, wherein the first wavelength is 1240 nanometers or greater.

20. The method of detecting hydrogen according to claim 13, wherein, (i) for light propagating within the hydrogen-sensing optical fiber at a wavelength of 1240 nanometers or greater, the hydrogen-sensing optical fiber does not exhibit significant irreversible hydrogen-induced attenuation losses after exposure to a hydrogen-rich atmosphere and (ii) the first wavelength is 1240 nanometers or greater.

21. The method of detecting hydrogen according to claim 13, wherein, (i) for light propagating within the hydrogen-sensing optical fiber at any wavelength between 1240 nanometers and 1244 nanometers inclusively, the hydrogen-sensing optical fiber does not exhibit significant irreversible hydrogen-induced attenuation losses after exposure to a hydrogen-rich atmosphere and (ii) the first wavelength is between 1240 nanometers and 1244 nanometers inclusively.

* * * * *